(12) United States Patent
Bernards et al.

(10) Patent No.: US 8,969,544 B2
(45) Date of Patent: Mar. 3, 2015

(54) COMBINED USE OF PRAME INHIBITORS AND HDAC INHIBITORS

(76) Inventors: René Bernards, Amsterdam (NL);
Mirjam Epping, Amsterdam (NL);
Liming Wang, Amsterdam (NL)

( * ) Notice: Subject to any disclaimer, the term of this patent is extended or adjusted under 35 U.S.C. 154(b) by 480 days.

(21) Appl. No.: 13/045,284

(22) Filed: Mar. 10, 2011

(65) Prior Publication Data

US 2013/0123327 A1    May 16, 2013

Related U.S. Application Data

(62) Division of application No. 10/587,023, filed as application No. PCT/EP2005/000937 on Jan. 27, 2005, now Pat. No. 7,928,081.

(30) Foreign Application Priority Data

Jan. 28, 2004 (GB) .................................. 0401876.8

(51) Int. Cl.
| | | |
|---|---|---|
| C07H 21/04 | (2006.01) | |
| A61K 31/7088 | (2006.01) | |
| A61K 31/16 | (2006.01) | |
| A61K 31/203 | (2006.01) | |
| A61K 45/06 | (2006.01) | |
| C12N 15/113 | (2010.01) | |
| A61K 31/18 | (2006.01) | |
| A61K 48/00 | (2006.01) | |

(52) U.S. Cl.
CPC ............. *A61K 31/7088* (2013.01); *A61K 31/16* (2013.01); *A61K 31/203* (2013.01); *A61K 45/06* (2013.01); *C12N 15/113* (2013.01); *A61K 31/18* (2013.01); *A61K 48/00* (2013.01); *C12N 2310/111* (2013.01); *C12N 2310/14* (2013.01); *C12N 2320/31* (2013.01)
USPC .......................................... 536/24.5; 514/44

(58) Field of Classification Search
None
See application file for complete search history.

(56) References Cited

U.S. PATENT DOCUMENTS 7,928,081 B2    4/2011   Bernards et al.

OTHER PUBLICATIONS

Partial International Search Report for PCT/EP2005/000937.
Ikeda et al., *Characterization of an antigen that is recognized on a melanoma showing partial HLA loss by CTL expressing an NK inhibitory receptor*, Immunity, vol. 6, No. 2, Feb. 1997, pp. 199-208, XP002216277.
Plumb et al., *Pharmacodynamic response and inhibition of growth of human tumor xenografts by the novel histone deacetylase inhibitor PXD101*, Molecular Cancer Therapeutics, vol. 2, No. 8, Aug. 2003, pp. 721-728, XP002372785.
Freemantle et al., *Retinoids in cancer therapy and chemoprevention: Promise meets resistance*, Oncogene, vol. 22, No. 47, Oct. 20, 2003, pp. 7305-7315, XP008061601.
Brummelkamp et al., *Stable Suppression of Tumorigenicity by Virus-Mediated RNA Interference*, Cancer Cell, vol. 2, No. 3, Sep. 2002, pp. 243-247, XP009006464.
Epping et al., *The Human Tumor Antigen Prame is a Dominant Repressor of Retinoic Acid Receptor Signaling*, Cell, vol. 122, No. 6, Sep. 23, 2005, pp. 835-847, XP008061580.
Tajeddine et al., *Tumor-associated antigen preferentially expressed antigen of melanoma (PRAME) induces caspase-independent cell death in vitro and reduces tumorigenicity in vivo*, Cancer Research, vol. 65, No. 16, Aug. 2005, pp. 7348-7355, XP002372786.
Product: sc-37322, Online Catalog of Santa Cruz Biotechnology, Inc., 2004, XP002372787.
Epping et al, "A functional genetic screen identifies retinoic acid signaling as a target of histone deacetylase inhibitors", PNAS, Nov. 6, 2007, vol. 104, No. 45, pp. 17777-17782.
Epping et al, "A functional genetic screen identifies retinoic acid signaling as a target of histone deacetylase inhibitors", PNAS, Nov. 6, 2007, vol. 104, No. 45, Supporting Figures (5 pages).
McCarthy, "PRAME in the frame", Nature Reviews Cancer, vol. 5, 2005, p. 839.
Doolan et al, "Prevalence and prognostic and predictive relevance of PRAME in breast cancer", Breast Cancer Res. Treat. 2008, vol. 109:359-365.
Tajeddine et al, "Tumor-Associated Antigen Preferentially Expressed Antigen of Melanoma (PRAME) Induces Caspase-Independent Cell Death In vitro and Reduces Tumorigenicity In vivo", Cancer Research 2005, vol. 65:7348-7355.

*Primary Examiner* — Kimberly Chong
(74) *Attorney, Agent, or Firm* — Nixon & Vanderhye P.C.

(57) ABSTRACT

The invention relates to the cancer antigen PRAME (PReferentially expressed Antigen in MElanoma) and its use in a method of treatment of a tumour which comprises administering to a subject in need of treatment an effective amount of an inhibitor of PRAME, in combination with a second agent selected from the group of an inhibitor of HDAC (an HDACi) and a retinoid.

2 Claims, 5 Drawing Sheets

SEQUENCE LISTING

<160> NUMBER OF SEQ ID NOS: 21

<210> SEQ ID NO 1
<211> LENGTH: 2067
<212> TYPE: DNA
<213> ORGANISM: Homo sapiens

<400> SEQUENCE: 1

```
gggaaaccga ctcctgggag cagggaggaa cgcgcgctcc agagacaact tcgcggtgtg      60
gtgaactctc tgaggaaaaa cacgtgcgtg gcaacaagtg actgagacct agaaatccaa     120
gcgttggagg tcctgaggcc agcctaagtc gcttcaaaat ggaacgaagg cgtttgtggg     180
```

```
gttccattca gagccgatac atcagcatga gtgtgtggac aagcccacgg agacttgtgg    240
agctggcagg gcagagcctg ctgaaggatg aggccctggc cattgccgcc ctggagttgc    300
tgcccaggga gctcttcccg ccactcttca tggcagcctt tgacgggaga cacagccaga    360
ccctgaaggc aatggtgcag gcctggccct tcacctgcct ccctctggga gtgctgatga    420
agggacaaca tcttcacctg gagaccttca agctgtgct tgatggactt gatgtgctcc    480
ttgcccagga ggttcgcccc aggaggtgga aacttcaagt gctggattta cggaagaact    540
ctcatcagga cttctggact gtatggtctg gaaacagggc cagtctgtac tcatttccag    600
agccagaagc agctcagccc atgacaaaga agcgaaaagt agatggtttg agcacagagg    660
cagagcagcc cttcattcca gtagaggtgc tcgtagacct gttcctcaag gaaggtgcct    720
gtgatgaatt gttctcctac ctcattgaga aagtgaagcg aaagaaaaat gtactacgcc    780
tgtgctgtaa gaagctgaag attttttgcaa tgcccatgca ggatatcaag atgatcctga    840
aaatggtgca gctggactct attgaagatt tggaagtgac ttgtacctgg aagctaccca    900
ccttggcgaa atttttctcct tacctgggcc agatgattaa tctgcgtaga ctcctcctct    960
cccacatcca tgcatcttcc tacatttccc cggagaagga agagcagtat atcgcccagt    1020
tcacctctca gttcctcagt ctgcagtgcc tgcaggctct ctatgtggac tctttatttt    1080
tccttagagg ccgcctggat cagttgctca ggcacgtgat gaaccccttg gaaaccctct    1140
caataactaa ctgccggctt tcggaagggg atgtgatgca tctgtcccag agtcccagcg    1200
tcagtcagct aagtgtcctg agtctaagtg gggtcatgct gaccgatgta agtcccgagc    1260
ccctccaagc tctgctggag agagcctctg ccaccctcca ggacctggtc tttgatgagt    1320
gtgggatcac ggatgatcag ctccttgccc tcctgccttc cctgagccac tgctcccagc    1380 ttacaaccctt aagcttctac gggaattcca tctccatatc tgccttgcag agtctcctgc    1440
agcacctcat cgggctgagc aatctgaccc acgtgctgta tcctgtcccc ctggagagtt    1500
atgaggacat ccatggtacc ctccacctgg agaggcttgc ctatctgcat gccaggctca    1560
gggagttgct gtgtgagttg gggcggccca gcatggtctg gcttagtgcc aaccctgtc    1620 ctcactgtgg ggacagaacc ttctatgacc cggagcccat cctgtgcccc tgtttcatgc    1680
ctaactagct gggtgcacat atcaaatgct tcattctgca tacttggaca ctaaagccag    1740
gatgtgcatg catcttgaag caacaaagca gccacagttt cagacaaatg ttcagtgtga    1800
gtgaggaaaa catgttcagt gaggaaaaaa cattcagaca aatgttcagt gaggaaaaaa    1860
aggggaagtt ggggatagge agatgttgac ttgaggagtt aatgtgatct ttggggagat    1920
acatcttata gagttagaaa tagaatctga atttctaaag ggagattctg gcttgggaag    1980
tacatgtagg agttaatccc tgtgtagact gttgtaaaga aactgttgaa aataaagaga    2040
agcaatgtga aaaaaaaaaa aaaaaaa                                        2067
```

<210> SEQ ID NO 2
<211> LENGTH: 21
<212> TYPE: DNA
<213> ORGANISM: Homo sapiens

<400> SEQUENCE: 2
ggtgcctgtg atgaattgtt c                                               21

<210> SEQ ID NO 3
<211> LENGTH: 68
<212> TYPE: DNA

<210> SEQ ID NO 3
<211> LENGTH: 68
<212> TYPE: DNA
<213> ORGANISM: Artificial sequence
<220> FEATURE:
<223> OTHER INFORMATION: Oligonucleotide

<400> SEQUENCE: 3
gatccccggt gcctgtgatg aattgttctt caagagagaa caattcatca caggcacctt    60
tttggaaa                                                              68

<210> SEQ ID NO 4
<211> LENGTH: 68
<212> TYPE: DNA
<213> ORGANISM: Artificial sequence
<220> FEATURE:
<223> OTHER INFORMATION: Oligonucleotide

<400> SEQUENCE: 4
agcttttcca aaaggtgcc tgtgatgaat tgttctctct tgaagaacaa ttcatcacag     60
gcaccggg                                                              68

<210> SEQ ID NO 5
<211> LENGTH: 509
<212> TYPE: PRT
<213> ORGANISM: Homo sapiens

<400> SEQUENCE: 5

```
Met Glu Arg Arg Arg Leu Arg Gly Ser Ile Gln Ser Arg Tyr Ile Ser
1               5                   10                  15

Met Ser Val Trp Thr Ser Pro Arg Arg Leu Val Glu Leu Ala Gly Gln
                20                  25                  30

Ser Leu Leu Lys Asp Glu Ala Leu Ala Ile Ala Ala Leu Glu Leu Leu
            35                  40                  45

Pro Arg Glu Leu Phe Pro Pro Leu Phe Met Ala Ala Phe Asp Gly Arg
        50                  55                  60

His Ser Gln Thr Leu Lys Ala Met Val Gln Ala Trp Pro Phe Thr Cys
65                  70                  75                  80

Leu Pro Leu Gly Val Leu Met Lys Gly Gln His Leu His Leu Glu Thr
                85                  90                  95

Phe Lys Ala Val Leu Asp Gly Leu Asp Val Leu Leu Ala Gln Glu Val
                100                 105                 110

Arg Pro Arg Arg Trp Lys Leu Gln Val Leu Asp Leu Arg Lys Asn Ser
            115                 120                 125

His Gln Asp Phe Trp Thr Val Trp Ser Gly Asn Arg Ala Ser Leu Tyr
        130                 135                 140

Ser Phe Pro Glu Pro Glu Ala Ala Gln Pro Met Thr Lys Lys Arg Lys
145                 150                 155                 160

Val Asp Gly Leu Ser Thr Glu Ala Glu Gln Pro Phe Ile Pro Val Glu
                165                 170                 175

Val Leu Val Asp Leu Phe Leu Lys Glu Gly Ala Cys Asp Glu Leu Phe
            180                 185                 190

Ser Tyr Leu Ile Glu Lys Val Lys Arg Lys Lys Asn Val Leu Arg Leu
        195                 200                 205

Cys Cys Lys Lys Leu Lys Ile Phe Ala Met Pro Met Gln Asp Ile Lys
    210                 215                 220

Met Ile Leu Lys Met Val Gln Leu Asp Ser Ile Glu Asp Leu Glu Val
225                 230                 235                 240

Thr Cys Thr Trp Lys Leu Pro Thr Leu Ala Lys Phe Ser Pro Tyr Leu
                245                 250                 255
```

-continued

```
Gly Gln Met Ile Asn Leu Arg Arg Leu Leu Ser His Ile His Ala
            260                 265                 270

Ser Ser Tyr Ile Ser Pro Glu Lys Glu Gln Tyr Ile Ala Gln Phe
        275                 280                 285

Thr Ser Gln Phe Leu Ser Leu Gln Cys Leu Gln Ala Leu Tyr Val Asp
    290                 295                 300

Ser Leu Phe Phe Leu Arg Gly Arg Leu Asp Gln Leu Leu Arg His Val
305                 310                 315                 320

Met Asn Pro Leu Glu Thr Leu Ser Ile Thr Asn Cys Arg Leu Ser Glu
                325                 330                 335

Gly Asp Val Met His Leu Ser Gln Ser Pro Ser Val Ser Gln Leu Ser
            340                 345                 350

Val Leu Ser Leu Ser Gly Val Met Leu Thr Asp Val Ser Pro Glu Pro
        355                 360                 365

Leu Gln Ala Leu Leu Glu Arg Ala Ser Ala Thr Leu Gln Asp Leu Val
    370                 375                 380

Phe Asp Glu Cys Gly Ile Thr Asp Gln Leu Leu Ala Leu Leu Pro
385                 390                 395                 400

Ser Leu Ser His Cys Ser Gln Leu Thr Thr Leu Ser Phe Tyr Gly Asn
                405                 410                 415

Ser Ile Ser Ile Ser Ala Leu Gln Ser Leu Leu Gln His Leu Ile Gly
            420                 425                 430

Leu Ser Asn Leu Thr His Val Leu Tyr Pro Val Pro Leu Glu Ser Tyr
        435                 440                 445

Glu Asp Ile His Gly Thr Leu His Leu Glu Arg Leu Ala Tyr Leu His
    450                 455                 460

Ala Arg Leu Arg Glu Leu Leu Cys Glu Leu Gly Arg Pro Ser Met Val
465                 470                 475                 480

Trp Leu Ser Ala Asn Pro Cys Pro His Cys Gly Asp Arg Thr Phe Tyr
                485                 490                 495

Asp Pro Glu Pro Ile Leu Cys Pro Cys Phe Met Pro Asn
            500                 505

<210> SEQ ID NO 6
<211> LENGTH: 18
<212> TYPE: PRT
<213> ORGANISM: Homo sapiens

<400> SEQUENCE: 6

Phe Pro Glu Pro Glu Ala Ala Gln Pro Met Thr Lys Lys Arg Lys Val
1               5                   10                  15

Asp Gly

<210> SEQ ID NO 7
<211> LENGTH: 13
<212> TYPE: PRT
<213> ORGANISM: Homo sapiens

<400> SEQUENCE: 7

Cys Gly Asp Arg Thr Phe Tyr Asp Pro Glu Pro Ile Leu
1               5                   10

<210> SEQ ID NO 8
<211> LENGTH: 5
<212> TYPE: PRT
<213> ORGANISM: Homo sapiens
```

```
<400> SEQUENCE: 8

Leu Asp Val Leu Leu
1               5

<210> SEQ ID NO 9
<211> LENGTH: 5
<212> TYPE: PRT
<213> ORGANISM: Homo sapiens

<400> SEQUENCE: 9

Leu Arg Arg Leu Leu
1               5

<210> SEQ ID NO 10
<211> LENGTH: 5
<212> TYPE: PRT
<213> ORGANISM: Homo sapiens

<400> SEQUENCE: 10

Leu Asp Gln Leu Leu
1               5

<210> SEQ ID NO 11
<211> LENGTH: 5
<212> TYPE: PRT
<213> ORGANISM: Homo sapiens

<400> SEQUENCE: 11

Leu Gln Ala Leu Leu
1               5

<210> SEQ ID NO 12
<211> LENGTH: 5
<212> TYPE: PRT
<213> ORGANISM: Homo sapiens

<400> SEQUENCE: 12

Leu Leu Ala Leu Leu
1               5

<210> SEQ ID NO 13
<211> LENGTH: 5
<212> TYPE: PRT
<213> ORGANISM: Homo sapiens

<400> SEQUENCE: 13

Leu Gln Ser Leu Leu
1               5

<210> SEQ ID NO 14
<211> LENGTH: 5
<212> TYPE: PRT
<213> ORGANISM: Homo sapiens

<400> SEQUENCE: 14

Leu Arg Glu Leu Leu
1               5

<210> SEQ ID NO 15
<211> LENGTH: 5
<212> TYPE: PRT
<213> ORGANISM: Artificial sequence
<220> FEATURE:
<223> OTHER INFORMATION: PRAME-deltaLXXLL mutant
```

```
<400> SEQUENCE: 15

Leu Asp Val Val Val
1               5

<210> SEQ ID NO 16
<211> LENGTH: 5
<212> TYPE: PRT
<213> ORGANISM: Artificial sequence
<220> FEATURE:
<223> OTHER INFORMATION: PRAME-deltaLXXLL mutant

<400> SEQUENCE: 16

Val Arg Arg Leu Leu
1               5

<210> SEQ ID NO 17
<211> LENGTH: 5
<212> TYPE: PRT
<213> ORGANISM: Artificial sequence
<220> FEATURE:
<223> OTHER INFORMATION: PRAME-deltaLXXLL mutant

<400> SEQUENCE: 17

Leu Asp Gln Val Val
1               5

<210> SEQ ID NO 18
<211> LENGTH: 5
<212> TYPE: PRT
<213> ORGANISM: Artificial sequence
<220> FEATURE:
<223> OTHER INFORMATION: PRAME-deltaLXXLL mutant

<400> SEQUENCE: 18

Val Gln Ala Leu Leu
1               5

<210> SEQ ID NO 19
<211> LENGTH: 5
<212> TYPE: PRT
<213> ORGANISM: Artificial sequence
<220> FEATURE:
<223> OTHER INFORMATION: PRAME-deltaLXXLL mutant

<400> SEQUENCE: 19

Leu Leu Ala Val Val
1               5

<210> SEQ ID NO 20
<211> LENGTH: 5
<212> TYPE: PRT
<213> ORGANISM: Artificial sequence
<220> FEATURE:
<223> OTHER INFORMATION: PRAME-deltaLXXLL mutant

<400> SEQUENCE: 20

Leu Gln Ser Val Val
1               5

<210> SEQ ID NO 21
<211> LENGTH: 5
<212> TYPE: PRT
<213> ORGANISM: Artificial sequence
<220> FEATURE:
<223> OTHER INFORMATION: PRAME-deltaLXXLL mutant

<400> SEQUENCE: 21
```

```
Leu Arg Glu Val Val
1           5
```

COMBINED USE OF PRAME INHIBITORS AND HDAC INHIBITORS

CROSS-REFERENCE TO RELATED APPLICATIONS

This application is a divisional of U.S. patent application Ser. No. 10/587,023, filed Jan. 9, 2007 now U.S. Pat No. 7,928,081, which is a U.S. national phase entry of International Patent Application No. PCT/EP2005/000937, filed Jan. 27, 2005, which designated the United States and claims priority to United Kingdom Patent Application No. GB 0401876.8, filed Jan. 28, 2004. All disclosures of the foregoing patent applications are incorporated by reference herein in their entireties.

BACKGROUND OF THE INVENTION

The present invention defines a new use for the known cancer antigen PRAME (PReferentially expressed Antigen in MElanoma), and in particular provides methods for the stratification of cancer patients based on PRAME expression and for the treatment of subjects with cancer by the inhibition of PRAME expression or activity.

Retinoic acid (RA) induces proliferation arrest, differentiation and apoptosis in a wide variety of cell types (Altucci, 2001; Freemantle, 2003). Defects in retinoic acid receptor (RAR) signalling, such as those caused by the RML-RARα and PLZF-RARα translocations in acute promyelocytic leukaemia, have been implicated in cancer (Altucci, 2001; Freemantle, 2003. Binding of RA to its receptor leads to release of co-repressor molecules and recruitment of co-activators to RAR, resulting in activation of transcription (Xu, 1999).

Acetylation and deacetylation of histones is associated with transcriptional events leading to cell proliferation and/or differentiation. Regulation of the function of transcription factors is also mediated through acetylation. Recent reviews of histone deacetylation include Kouzarides, 1999 and Pazin et al., 1997.

The correlation between the acetylation status of histones and the transcription of genes has been known for over 30 years (see, for example, Howe et al., 1999). Certain enzymes, specifically acetylases (e.g., histone acetyltransferase, HAT) and deacetylases (e.g., histone deacetylase, HDAC), which regulate the acetylation state of histones have been identified in many organisms and have been implicated in the regulation of numerous genes, confirming the link between acetylation and transcription. See, for example, Davie, 1998. In general, histone acetylation correlates with transcriptional activation, whereas histone deacetylation is associated with gene repression.

A growing number of histone deacetylases (HDACs) have been identified (see, for example, Ng and Bird, 2000). The first deacetylase, HDAC1, was identified in 1996 (see, for example, Tauton et al., 1996). Subsequently, two other nuclear mammalian deacetylases were found, HDAC2 and HDAC3 (see, for example, Yang et al., 1996, 1997, and Emiliani et al., 1998). See also, Grozinger et al., 1999; Kao et al., 2000; and Van den Wyngaert et al., 2000.

HDACs function as part of large multiprotein complexes, which are tethered to the promoter and repress transcription. Well characterised transcriptional repressors such as Mad (Laherty et al., 1997), pRb (Brehm et al., 1998), nuclear receptors (Wong et al., 1998) and YY1 (Yang et al., 1997) associate with HDAC complexes to exert their repressor function.

The study of inhibitors of histone deacetylases indicates that these enzymes play an important role in cell proliferation and differentiation. The inhibitor Trichostatin A (TSA) (Yoshida et al., 1990a) causes cell cycle arrest at both G1 and G2 phases (Yoshida and Beppu, 1988), reverts the transformed phenotype of different cell lines, and induces differentiation of Friend leukaemia cells and others (Yoshida et al., 1990b). TSA (and SAHA) have been reported to inhibit cell growth, induce terminal differentiation, and prevent the formation of tumours in mice (Finnin et al., 1999).

The activity of HDACs and HATS (Histone Acetyl Transferases) is frequently deregulated in cancer and one of the ways in which these enzymes are involved in cancer is in the repression of retinoic acid receptor signalling.

The clear involvement of HDACs in the control of cell proliferation and differentiation suggests that aberrant HDAC activity may play a role in cancer. The most direct demonstration that deacetylases contribute to cancer development comes from the analysis of different acute promyelocytic leukemias (APL). In most APL patients, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation, The RARα fusion proteins occurring in APL patients are no longer responsive to physiological levels of RA and they interfere with the expression of the RA-inducible genes that promote myeloid differentiation. This results in a clonal expansion of promyelocytic cells and development of leukaemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL patients. (See, for example, Kitamura et al., 2000; David et al., 1998; Lin et al., 1998).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida and Horinouchi, 1999). A number of HDAC inhibitors have been studied in animal models of cancer. They reduce tumour growth and prolong the lifespan of mice bearing different types of transplanted tumours, including melanoma, leukaemia, colon, lung and gastric carcinomas, etc. (Ueda et al., 1994; Kim et al., 1999).

Thus, although HDAC inhibitors (HDACi) are a promising new class of anti-cancer drug, the molecular basis for their selective growth-inhibitory activity on cancer cells is at present unclear.

PRAME was first identified as an antigen in human melanoma that triggers cytotoxic T cell-mediated anti-tumour immune responses (Ikeda et al, 1997). PRAME is also overexpressed in a variety of other human malignancies, including acute and chronic leukemias, non-small-cell lung carcinoma, head and neck cancer, renal carcinoma, and its expression is prognostic for a poor clinical outcome in breast cancer (Ikeda, 1997; van't Veer 2002; van Hazen, 1998; Neumann 1998; Boon, 2003). However, no function for PRAME has been described to date.

The present invention demonstrates that PRAME expression inhibits retinoic acid-induced differentiation, growth arrest and apoptosis and that PRAME is, therefore, a dominant repressor, or negative regulator, of RAR signalling. The invention also shows that PRAME suppresses the HDACi-mediated activation of RAR signalling. These discoveries of a function for PRAME have opened up a new avenue for the treatment of cancer, via the suppression of PRAME, as well as enabling the stratification of subjects prior to treatment with known anti-cancer treatments, such as retinoids and HDACi's.

SUMMARY OF THE INVENTION

Accordingly, in its first aspect, the present invention provides a method of treatment of a tumour which comprises administering to a subject in need of treatment an effective amount of an inhibitor of PRAME, in combination with a second agent selected from the group of an inhibitor of HDAC (an HDACi) and a retinoid.

In a further aspect, the method provides an inhibitor of PRAME and a second agent selected from the group of an inhibitor of HDAC (an HDACi) and a retinoid, as a combined preparation for simultaneous, separate or sequential use in therapy.

The invention also provides the use of an inhibitor of PRAME in combination with an HDACi or a retinoid for the manufacture of a medicament as a combined preparation for simultaneous, separate or sequential use in the treatment of a tumour.

The invention further provides the use of an HDACi, or a retinoid, for treating a tumour in a subject, wherein the subject has received treatment so as to suppress the level of PRAME in the tumour at the time of HDACi or retinoid administration.

The invention further provides a methods of stratification of patients based on PRAME levels. This stratification may be used in diagnosis or prognosis for selection of patients for treatment, or to determine the likely effectiveness of treatment.

The present invention also provides an assay for an inhibitor of an interaction between PRAME and a retinoic acid receptor (RAR) which comprises bringing together:
(i) a candidate inhibitor; and
(ii) a PRAME protein and a RAR protein; and
determining if the putative inhibitor is capable of preventing an interaction between said PRAME and RAR proteins.

DETAILED DESCRIPTION OF THE INVENTION

Inhibitor of PRAME

Figure 1:
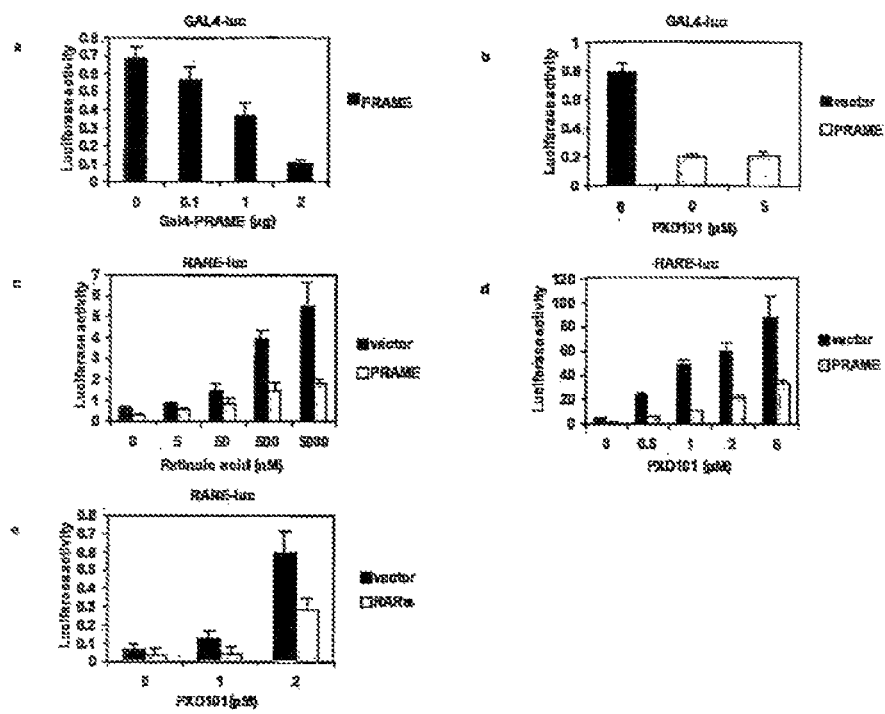
FIG. 1: PRAME is a repressor of RAR signalling. a, 293 cells were transfected with a GAL4-PRAME chimeric construct and a GAL4-luciferase reporter. b, 293 cells were transfected as in a, and were treated with PXD101. c, Ras $^{V12}$ MEFs were transfected with a RA-responsive luciferase reporter (RARE-luc) and either is PRAME or empty vector, and treated with RA. d, Ras $^{V12}$ MEFs were transfected as in c, and treated with PXD101. e, Ras $^{V12}$ MEFs were transfected with RARE-luciferase and either RARα or empty vector, and were treated with PXD101.

An inhibitor of PRAME includes any compound capable of either preventing expression of PRAME or of preventing PRAME when expressed from exerting its normal activity. Normal activity, as used in this respect, refers to any activity performed by the PRAME expression product in the human or animal body. Typically such activities include the repression of transcription and/or interaction with RAR.

A preferred inhibitor of PRAME is an interfering RNA (RNAi). RNA interference is the process of sequence-specific, post-transcriptional gene silencing in animals and plants, initiated by double-stranded RNA (dsRNA) that is homologous in sequence to the silenced gene. RNA interference (RNAi) is a process whereby the introduction of double stranded RNA (dsRNA) into a cell inhibits gene expression post-translationally, in a sequence dependent fashion. This process is also known as post-transcriptional gene silencing. Current models of RNAi indicate that it is mediated by short (typically 20-25 nucleotides) dsRNAs known as 'small interfering RNAs' (siRNA). It appears that dsRNA is cleaved in the cell to create siRNAs. siRNAs are then incorporated into an RNA-induced silencing complex (RISC), guiding the complex to the homologous endogenous mRNA. The activated RISC then cleaves the mRNA transcript, resulting in the destruction of the mRNA in a cell which is homologous to the siRNAs. The siRNAs are re-cycled. In this way, a relatively small number of siRNAs can selectively destroy a large excess of cellular mRNA.

To induce RNA interference in a cell, dsRNA may be introduced into the cell via a transgene, plasmid or virus which brings about expression of the siRNA in the cell. Alternatively, siRNA may be synthesised and introduced directly into the cell, optionally in the form of a pharmaceutical composition.

The complementary strands of the siRNA may be between 10 nucleotides (nt) and 30 nt in length, preferably between 20 nt and 25 nt. Preferably, the siRNA is 20, 21 or 22 nt in length. Generally, the nucleotides form a complementary double strand which may have short overhangs of one or two nt.

The siRNA sequence may be based on a contiguous sequence of 10-30 nucleotides from the cDNA sequence of PRAME. The human cDNA sequence of PRAME is available GenBank accession no. BC014074 and is shown herein as SEQ ID NO:1. It is known that certain residues of SEQ ID NO:1 are sites of single nucleotide polymorphisms, namely residues 177 (T/C), 621 (C/A), 924 (T/C), 1421 (T/C), 1685 (T/C) and 1966 (T/A) and thus siRNAs designed to target regions including any of these SNPs may include one or other of the SNP residues, or the siRNA may be a mixture thereof. Preferably however the siRNA will be targeted to a region of the sequence which does not contain a known SNP.

The siRNA may be used to target a coding or non-coding region of SEQ ID NO:1. The coding region comprises 159 to 1688 of SEQ ID NO:1. A particular region of SEQ ID NO:1 which may be targeted is the 21 nucleotide region of 714-734, shown below as SEQ ID NO:2.

siRNA molecules may be synthesized using standard solid or solution phase synthesis techniques which are known in the art. Linkages between nucleotides may be phosphodiester bonds or alternatives, for example, linking groups of the formula P(O)S, (thioate); P(S)S, (dithioate); P(O)NR'2; P(O)R'; P(O)OR6; CO; or CONR'2. wherein R is H (or a salt) or alkyl (1-12C) and R6 is alkyl (1-9C) is joined to adjacent nucleotides through —O— or —S—.

Modified nucleotide bases can be used in addition to the naturally occurring bases, and may confer advantageous properties on siRNA molecules containing them.

For example, modified bases may increase the stability of the siRNA molecule, thereby reducing the amount required for silencing. The provision of modified bases may also provide siRNA molecules which are more, or less, stable than unmodified siRNA.

The term 'modified nucleotide base' encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include alkylated purines and pyrimidines, acylated•purines and pyrimidines, and other heterocycles. These classes of pyrimidines and purines are known in the art and include pseudoisocytosine, N4,N4-ethanocytosine, 8-hydroxy-N-6-methyladenine, 4-acetylcytosine, 5-(carboxyhydroxylmethyl) uracil, 5 fluorouracil, 5-bromouracil, 5-carboxymethylaminomethyl-2-thiouracil, 5-carboxymethyl-aminomethyl uracil, dihydrouracil, inosine, N6-isopentyl-adenine, 1-methyladenine, 1-methylpseudouracil, 1-methyl-guanine, 2,2-dimethylguanine, 2-methyladenine, 2-methylguanine, 3-methylcytosine, 5-methylcytosine, N6-methyladenine, 7-methyl-guanine, 5-methylaminomethyl uracil, 5-methoxy amino methyl-2-thiouracil, 5-methoxycarbonylmethyluracil, 5-methoxyuracil, 2 methylthio-N-6-isopentenyladenine, uracil-5-oxyacetic acid methyl ester, psueouracil, 2-thiocytosine, 5-methyl-2 thiouracil, 2-thiouracil, 4-thiouracil, 5-methyluracil, N-uracil-5-oxyacetic acid methylester, uracil 5-oxyacetic acid, queosine, 2-thiocytosine, 5-propyluracil, 5-propylcytosine, 5-ethyluracil, 5ethylcytosine, 5-butyluracil, 5-pentyluracil, 5-pentylcytosine, 2,6,diaminopurine, methylpsuedouracil, 1-methylguanine, 1-methylcytosine.

Alternatively, siRNA molecules or longer dsRNA molecules may be made recombinantly by transcription of a nucleic acid sequence, preferably contained within a vector as described below. Such a vector may be one designed to be introduced into a target tumour cell so as to produce an siRNA in vivo. Where the siRNA is produced by recombinant means, the two strands of the siRNA may be produced in separate transcripts. More desirably however the siRNA may be made in the form of a single transcript which forms a hairpin loop structure comprising a double-stranded siRNA sequence, for example as described in Brummelkamp et al, Science 2002.

Thus it will be understood that an inhibitor of PRAME includes a recombinant vector capable of expressing an siRNA in a target tumour cell. Such a vector may comprise a sequence coding for the siRNA operably linked to a promoter. The promoter may be any promoter suitable for the transcription of the siRNA, such as a eukaryotic promoter. Such a promoter may be an RNA gene promoter, such as a promoter which produces a small RNA transcript which preferably has a defined 3' end lacking a polyA tail. A preferred such promoter is the polymerase-III H1 gene RNA promoter.

The vector may be a viral vector, such as an adenovirus, herpes virus, vaccinia virus or retrovirus vector. Various viral vector systems for delivery to a human or animal subject are known in the art, for example as described in U.S. Pat. Nos. 6,228,844 and 6,339,068, the contents of which are incorporated herein by reference. The vector will include the siRNA-encoding sequence operably linked to a promoter, as a construct carried by the vector either in place of a native vector gene or inserted as additional DNA within the vector.

Further inhibitors of PRAME may be identified using the assay described herein below which forms a further aspect of the present invention.

Inhibitor of HDAC

HDAC inhibitors suitable for use in the treatment of cancer are known in the art. Typical HDACi include trichostatin A (TSA), trapoxin, suberoylanilide hydroxamic acid (SAHA), and phenylbutyrate, which have been reported to act, at least in part, by inhibiting histone deacetylase (see, e.g., Yoshida et al., 1990; Richon et al., 1998; Kijima et al., 1993).

Additionally, diallyl sulfide and related molecules (see, e.g., Lea et al., 1999), oxamflatin (see, e.g., Kim et al., 1999; Sonoda et al., 1996), MS-27-275, a synthetic benzamide derivative (see, e.g., Saito et al., 1999; Suzuki et al., 1999; note that MS-27-275 was later re-named as MS-275), butyrate derivatives (see, e.g., Lea and Tulsyan, 1995), FR901228 (see, e.g., Nokajima et al., 1998), depudecin (see, e.g., Kwon et al., 1998), and m-carboxycinnamic acid bishydroxamide (see, e.g., Richon et al., 1998) have been reported to inhibit histone deacetylases. In vitro, some of these compounds are reported to inhibit the growth of fibroblast cells by causing cell cycle arrest in the G1 and G2 phases, and can lead to the terminal differentiation and loss of transforming potential of a variety of transformed cell lines (see, e.g., Richon et al, 1996; Kim et al., 1999; Yoshida et al., 1995; Yoshida & Beppu, 1988). In vivo, phenybutyrate is reported to be effective in the treatment of acute promyelocytic leukemia in conjunction with retinoic acid (see, e.g., Warrell et al., 1998). SAHA is reported to be effective in preventing the formation of mammary tumours in rats, and lung tumours in mice (see, e.g., Desai et al., 1999).

A preferred class of inhibitors are those described in the following publications, the contents of which are incorporated herein by reference:

Watkins, C., et al., 2002, "Carbamic acid compounds comprising a sulfonamide linkage as HDAC inhibitors," published international (PCT) patent application number WO 02/30879 (PCT/GB01/04326) published 18 Apr. 2002;

Watkins, C., et al., 2002, "Carbamic acid compounds comprising an ether linkage as HDAC inhibitors," published international (PCT) patent application number WO 02/26703 (PCT/GB01/04327) published 4 Apr. 2002;

Watkins, C., et al., 2002, "Carbamic acid compounds comprising an amide linkage as HDAC inhibitors," published international (PCT) patent application number WO 02/26696 (PCT/GB01/04329) published 4 Apr. 2002; and Watkins, C., et al., 2003, "Carbamic acid compounds comprising a piperazine linkage as HDAC inhibitors," published international (PCT) patent application number WO03/082288 (PCT/GB03/01463) published 9 Oct. 2003.

A particularly preferred compound is known as PXD101 (N-hydroxy-3-(3-phenylsulfamoyl-phenyl)-acrylamide), the structure of which is:

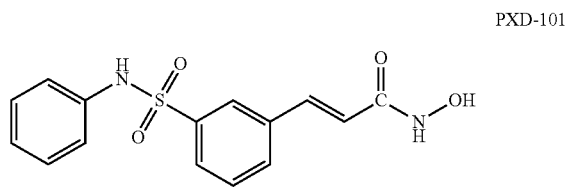 [SMILES: O=C(/C=C/c1cccc(S(=O)(=O)Nc2ccccc2)c1)NO]

PXD-101

This compound, or a pharmaceutically acceptable salt thereof, may be used in accordance with the present invention.

Retinoid

Compounds of retinoid type are compounds with a biological activity profile similar to that of all-trans-retinoic acid or 9-cis-retinoic acid, which compounds themselves may be used in the practice of the invention. These compounds can modify the expression of genes by means of receptors of the retinoic acid family, such as the RARs and RXRS. Thus, retinoids may exhibit activity in the test of differentiation of mouse embryonic teratocarcinoma cells (F9) (Strickland et al 1983) and/or in the test of inhibition of ornithine decarboxylase after induction with TPA in mice (Verma et al, 1978). These tests show the activities of these compounds in the fields of cell differentiation and cell proliferation, respectively.

A wide variety of retinoids are known in the art. For example, US patent application 20030055110, the contents of which are incorporated herein by reference, describes numerous retinoid compounds. The following compounds in particular were found to have activity of the RAR receptor antagonist type: 4-(4-(6-Methoxymethoxy-4'-methylbiphenyl-2-yl)but-3-en-1-ynyl)benzoic acid; 4-(4-(6-Methoxy-4'-methylbiphenyl-2-yl)but-3-en-1-ynyl)benzoic acid; 4-(6-Methoxyethoxymethoxy-7-(1-adamantyl)-2-naphthyl) salicylic acid; (E)-4-[4-(5-Methoxymethoxy-4'-methylbiphenyl-2-yl)but-3-en-1-ynyl]-benzoic acid; 4-[(4-(3-Methoxy-4'-methylbiphenyl-2-yl)but-3-en-1-ynyl] benzoic acid; 2-Methoxymethoxy-2'-(5,5,8,8-tetramethyl-5,6,7,8-tetrahydronaphthalen-2-yl) [1,1,4'1"]terphenyl-4"-carboxylic is acid; 4-[(4-(4'-Methylbiphenyl-2-yl)but-3-en-1-ynyl]benzoic acid; and 4-(4-(4'-Propylbiphenyl-2-yl)but-3-en-1-ynyl]benzoic acid.

Retinoid compounds such as these and others which exhibit activity at the RAR receptor (by which is, meant causing the receptor to induce expression of a RA-responsive gene, for example the RARβ gene as described herein), may be suitable for use in the present invention.

Treatment of a Tumour

The present invention may be applied to the treatment of a wide variety of tumours, particularly those which are associated with over-expression of HDAC, for example as a result of gene amplification or loss of regulation of the HDAC gene.

Tumours in which such over-expression may occur include melanomas, acute and chronic leukemias, non-small-cell lung carcinoma, head and neck cancer, renal carcinoma, and breast cancer.

By "treatment", it will be understood that this includes any intervention designed to alleviate the condition of the patient, e.g. by slowing down the rate of tumour progression, by providing an adjunct to other tumour therapies including surgery, by stabilizing the tumour or achieving partial or complete remission of the tumour.

Administration

The present findings indicate that the use of a PRAME inhibitor (PRAMEi) will allow HDAC inhibitors or retinoids to be used more effectively, where the PRAME inhibitor is administered with the HDACi or retinoid. Where reference is made to the administration of an HDACi or a retinoid, the invention also includes the administration of both.

By "simultaneous" administration, it is meant that the PRAMEi and the HDACi (or retinoid) are administered to a subject in a single dose by the same route of administration.

By "separate" administration, it is meant that the PRAMEi and the HDACi (or retinoid) are administered to a subject by two different routes of administration which occur at the same time. This may occur for example where one agent is administered by infusion and the other is given orally during the course of the infusion.

By "sequential" it is meant that the two agents are administered at different points in time, provided that the activity of the first administered agent is present and ongoing in the subject at the time the second agent is administered. For example, the PRAMEi may be administered first, such that the amount of PRAME protein in the tumour cells of the subject is reduced at the point in time when the HDACi and/or retinoid is administered.

Generally, a sequential dose will occur such that the second of the two agents is administered within 48 hours, preferably within 24 hours, such as within 12, 6, 4, 2 or 1 hour(s) of the first agent.

The agents will be formulated appropriately for their desired route of administration. The agent or pharmaceutical composition comprising the agent may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, as subarachnoid, and intrasternal; by implant of a depot or reservoir, for example, subcutaneously or intramuscularly.

The amount of a PRAMEi, RDACi and retinoid to be administered will ultimately be at the discretion of the physician taking into account the age and status of the subject, and the particular activity of the agent being administered. Administration in vivo can be effected in one dose, continuously or intermittently throughout the course of treatment. Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being, selected by the treating physician.

For example, where the PRAME is an siRNA, doses of siRNA may be in the range of from 0.001 μg to 100 g mg/kg body weight per dose. Doses may be administered daily or at other intervals determined by the physician. Where the siRNA is delivered to the site of a tumour in the form of a vector, the dose may be in the range of from $10^5$ to $10^8$ copies of the vector, which where the vector is in the form of a viral vector, may equate to the number of viral particles. For HDACi compounds the dose may be in the range of from 0.1 to about 250 mg per kilogram body weight of the subject per day. Retinoids may be administered in the range of dosages of the order of from 0.05 to 10 mg/kg/day, preferably 0.1 to 7.5 mg/kg/day, more preferably 0.1 to 2 mg/kg/day, administered once or, in divided doses, 2 to 4 times per day.

Administration to Prior-Treated Subject.

In a particular aspect, the invention relates to the use of an HDACi or a retinoid for the treatment of a novel subject type, namely a subject in whom the level of expression of PRAME in a tumour present in said subject has been suppressed by medical treatment at the time of HDACi or retinoid treatment.

The suppression of expression of PRAME may have been achieved by use of a PRAMEi as described herein. The patient will be one in which the PRAMEi has been administered recently enough so as to enhance the efficacy of the HDACi or retinoid, compared to the efficacy without the prior treatment. Desirably, the patient will have been treated with the PRAMEi within the previous 48, preferably 24, more preferably 12, such as 6, 4, 2 or 1 hour(s).

In one embodiment, the patient may be characterised as a patient in which PRAME siRNA is present in the body of the patient.

Stratification and Selection of Subjects

The present findings also allow the stratification and/or selection of subjects for treatment with a HDACi or retinoid.

In this aspect of the invention, it will be necessary to first establish or obtain data from a cohort (e.g. at least 20) existing tumour patients to determine the level of PRAME expression in their tumour. The level of expression may be determined at the level of RNA expression, e.g. using RT-PCR, or at the level of protein expression, e.g. using an antibody-based approach. Such methods are known per se in the art. The expression levels will be distributed between low, intermediate and high values. It will be appreciated that what is determined to be of a low, intermediate and high value will be to some extent an arbitrary designation depending upon the criteria applied by any one particular treatment centre, in a similar manner to, for example, biochemical markers used in prenatal diagnoses. However this does not prevent the method being practiced to the extent that the levels of PRAME can be determined in new subjects and compared to the collected data to establish predictions or dosings in accordance with the invention as set out herein below.

In one aspect, the present invention may be used to predict the effectiveness of a course of treatment with HDACi or a retinoid, or to select patient in which treatment with HDACi or a retinoid is more likely to be effective.

Accordingly in one aspect the invention provides a method comprising:
determining the level of expression of PRAME in a tumour of a subject;
comparing said level to the levels previously determined in a cohort of patients; and
treating said patient with a HDACi or a retinoid if said level is indicative of low expression.

It will be understood that the step of comparing may be performed on historic data, and that it is not necessary to repeat the determination for that cohort each time the above method is practiced.

By "low expression" it is preferably meant a level in the lower one-third, preferably the lower quartile of the distribution of the cohort.

The cohort to which reference is made is desirably matched for one or more of tumour type, age, sex or severity of disease.

In another aspect the invention provides a method comprising:
determining the level of expression of PRAME in a tumour of a subject;
comparing said level to the levels previously determined in a cohort of patients; and
treating said patient with a PRAMEi and one or both of an HDACi or a retinoid if said level is indicative of high expression.

By "high expression" it is preferably meant a level in the upper one-third, preferably the upper quartile of the distribution of the cohort.

In a similar manner, the invention may also be used to determine the frequency or amount of HDACi or retinoid administered to a patient, with more frequent or higher doses being administered to subjects with moderate to high levels of PRAME expression.

Assay Methods

In another aspect, the finding that PRAME interacts directly with the RAR provides a novel target for agents capable of modulating the growth, differentiation and vitality of cells.

Accordingly, candidate inhibitors of the interaction between PRAME and RAR are identified by a method comprising bringing together:
a candidate inhibitor; and
a PRAMEprotein and a RAR protein; and
determining if the candidate inhibitor is capable of preventing an interaction between said PRAME and RAR proteins.

For the purposes of this aspect of the invention, a PRAME protein will comprise a eukaryotic, preferably mammalian, for example a rodent (e.g. murine) or primate, e.g. human PRAME protein or a fragment thereof capable of forming a complex with a full length wild-type RAR protein, particularly human RAR.

Human PRAME protein is encoded by SEQ ID NO:1 shown herein. Proteins from other species may also be used, and obtained for example by homology searches of databases of genome sequences where such are available, or by recombinant molecular DNA techniques such as utilizing all or part of SEQ ID NO:1 as a probe against a genomic or cDNA library from a species of interest.

Fragments of PRAME will preferably comprise at least one of the seven "LXXLL" sequences identified herein, such as at least 2, 3, 4, 5 or 6 such sequences. Fragments may be at least 100, such as at least 200, e.g. at least 300, for example at least 400 amino acids in size. Fragments of these preferred sizes will desirably contain the above-mentioned preferred numbers of LXXLL motifs.

For the purposes of this aspect of the invention, a retinoic acid receptor alpha (RAR) protein will comprise a eukaryotic, preferably mammalian, for example a rodent (e.g. murine) or primate, e.g. human RAR protein or a fragment thereof capable of forming a complex with a full length wild-type PRAME protein, particularly human PRAME. The protein may be the alpha 1 or alpha 2 isoform.

A number of different RAR alpha proteins are available on public databases. Human RAR-alpha is SwissProt accession P10276, and murine is SwissProt P11416. The rat alpha 2 isoform is Genbank accession AAC23439.1. Non-mammalian versions of the protein have been characterised in chick (SwissProt Q90966), *Xenopus* (SwissProt P51126) and pufferfish (SwissProt Q9W5Z3).

Fragments may be at least 100, such as at least 200, e.g. at least 300, for example at least 400 amino acids in size.

Assays according to the invention may be performed in any format available to the person skilled in the art. The precise format of the assay of the invention may be varied by those of skill in the art using routine skill and knowledge.

For example, the interaction between a PPAME protein and an RAR may be studied by labelling one with a detectable label and bringing it into contact with the other which has been immobilised on a solid support. Suitable detectable labels include $^{35}$S-methionine which may be incorporated into recombinantly produced PRAME and/or RAR. The recombinantly produced PRAME and/or RAR may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above the putative modulator compound can be assayed by determining its ability to modulate the amount of labelled PRAME or RAR which binds to the immobilized GST-RAR or GST-PRAME, as the case may be. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

Alternatively an antibody attached to a solid support and directed against one of PRAMS or RAR may be used in place of GST to attach the molecule to the solid support. Antibodies against PRAME and RAR may be obtained in a variety of ways known as such in the art, and as discussed herein.

In an alternative mode, one of PRAME and RAR may be labelled with a fluorescent donor moiety and the other labelled with an acceptor which is capable of reducing the emission from the donor. This allows an assay according to the invention to be conducted by fluorescence resonance energy transfer (FRET). In this mode, the fluorescence signal of the donor will be altered when PRAME and RAR interact. The presence to a candidate modulator compound which modulates the interaction will increase the amount of unaltered fluorescence signal of the donor.

FRET is a technique known per se in the art and thus the precise donor and acceptor molecules and the means by which they are linked to PRAME and RAR may be accomplished by reference to the literature.

Suitable fluorescent donor moieties are those capable of transferring fluorogenic energy to another fluorogenic molecule or part of a compound and include, but are not limited to, coumarins and related dyes such as fluoresceins, rhodols and rhodamines, resorufins, cyanine dyes, bimanes, acridines, isoindoles, dansyl dyes, aminophthalic hydrazines such as luminol and isoluminol derivatives, aminophthalimides, aminonaphthalimides, aminobenzofurans, aminoquinolines, dicyanohydroquinones, and europium and terbium complexes and related compounds.

Suitable acceptors include, but are not limited to, coumarins and related fluorophores, xanthenes such as fluoresceins, rhodols and rhodamines, resorufins, cyanines, difluoroboradiazaindacenes, and phthalocyanines.

A preferred donor is fluorescein and preferred acceptors include rhodamine and carbocyanine. The isothiocyanate derivatives of these fluorescein and rhodamine, available from Aldrich Chemical Company Ltd, Gillingham, Dorset, UK, may be used to label PRAME and RAR. For attachment of carbocyanine, see for example Guo et al, J. Biol. Chem., 270; 27562-8, 1995.

The above assay formats may also be used to determine the ability of a putative modulator compound to modulate the interaction of PRAME with RAR. Such assays are optionally performed in the presence of a retinoid compound, such as retinoic acid.

Assays of the invention may also be performed in vivo. Such an assay may be performed in any suitable host cell, e.g a bacterial, yeast, insect or mammalian host cell. Yeast and mammalian host cells are particularly suitable. a To perform such an assay in vivo, constructs capable of expressing PRAME and RAR and a reporter gene construct may be introduced into the cells. This may be accomplished by any suitable technique, for example calcium phosphate precipitation or electroporation. The three constructs may be expressed transiently or as stable episomes, or integrated into the genome of the host cell.

In vivo assays may also take the form of two-hybrid assays wherein PRAME and RAR are expressed as fusion proteins, one being a fusion protein comprising a DNA binding domain (DBD), such as the yeast GAL4 binding domain, and the other being a fusion protein comprising an activation domain, such as that from GAL4 or VP16. In such a case the host cell (which again may be bacterial, yeast, insect or mammalian, particularly yeast or mammalian) will carry a reporter gene construct with a promoter comprising a DNA binding elements compatible with the DOD. The reporter gene may be a reporter gene as disclosed above. The promoters for the genes may be those discussed above.

PRAME and RAR and the reporter gene, may be introduced into the cell and expressed transiently or stably.

Candidate inhibitor compounds may be natural or synthetic chemical compounds used in drug screening programmes. Extracts of plants, microbes or other organisms, which contain several characterised or uncharacterised components, may also be used. Combinatorial library technology (including solid phase synthesis and parallel synthesis methodologies) provides an efficient way of testing a potentially vast number of different substances for the ability to modulate an interaction. Such libraries and their use are known in the art for all manner of natural products, small molecules and peptides, among others. Many such libraries are commercially available and sold for drug screening programmes of the type now envisaged by the present invention.

A further class of candidate inhibitor comprises antibodies or binding fragments thereof which bind a protein target.

Examples of antibody fragments, capable of binding an antigen or other binding partner, are the Fab fragment consisting of the VL, VH, C1 and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included. An antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. Such a technique allows the rapid production of antibodies against an antigen, and these antibodies may then be screening in accordance with the invention.

Another class of candidate molecules is peptides, based upon a fragment of the protein sequence to be inhibited. In particular, fragments of the protein corresponding to portions of the protein which interact with other proteins or with DNA, may be a target for small peptides which act as competitive inhibitors of protein function. Such peptides may be for example from 5 to 20 amino acids in length.

The peptides may also provide the basis for design of mimetics. Such mimetics will be based upon analysis of the peptide to determine the amino acid residues or portions of their side chains essential and important for biological activity to define a pharmacophore followed by modelling of the pharmacophore to design mimetics which retain the essential residues or portions thereof in an appropriate three-dimensional relationship. Various computer-aided techniques exist in the art in order to facilitate the design of such mimetics.

Inhibitors obtained in accordance with these aspects of the present invention may be used in methods of treating a cancer in a subject.

The present invention therefore also provides a pharmaceutical composition comprising an inhibitor of the interaction between PRAME and RAR together with a pharmaceutically acceptable carrier therefor.

Generally, the inhibitor will be formulated with one or more pharmaceutically acceptable carriers suitable for a chosen route of administration to a subject. For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc, a inhibitor and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound(s) in an amount effective to alleviate the symptoms of the subject being treated.

Routes of administration may depend upon the precise condition being treated, though since endothelial cells form the lining of the vasculature, administration into the blood stream (e.g. by i.v. injection) is one possible route.

In addition, the present invention provides an inhibitor of the interaction between PRAMS and RAR for use in therapy.

Furthermore, the present invention provides the use of an inhibitor of the interaction between PRAME and RAR in the manufacture of a medicament for the treatment of a cancer.
Methods and Experimental In order to address the molecular basis for the selective growth-inhibitory activity of HDACi on cancer cells, we performed a functional genetic screen to identify genes that confer resistance to a small-molecule HDACi, named PXD101 (Plumb et al, 2003). Oncogenic $RAS^{V12}$-transformed mouse embryonic fibroblasts ($RAS^{V12}$-MEFs) were infected with a high complexity retroviral cDNA expression library derived from human K562 erythroleukemia cells and exposed to 1 µM PXD101 for three to weeks. HDACi-resistant colonies appeared at low frequency only after infection with cDNA expression library. Integrated proviruses were mobilized from PXD101-resistant colonies by Moloney virus super-infection as described (Jacobs et al, 2000). After second round selection, cDNA inserts were recovered by PCR and identified by DNA sequence analysis. Using this approach, we identified full-length cDNAs encoding the human melanoma tumour antigen PRAME (PReferentially expressed Antigen in MElanoma (Ikeda et al, 1997) and Retinoic Acid Receptor alpha (RARα) as cDNAs that allow continuous proliferation in the presence of 1 µM PXD101. PRAME also rescues these cells from growth arrest by a related HDACi, Trichostatin A at a concentration of 0.1 µM.

PRAME expression by retroviral infection of Ras $^{V12}$ MEFs was compared to endogenous PRAME expression levels in the human melanoma cell lines FM6, SK23, 453A0, A375, FM3 and D10. Cell extracts were immunoblotted for PRAME and CDK4 (as a control). The level of PRAME required to confer resistance to HDACi in the $RAS^{V12}$-MEFs is comparable to that seen in several human melanoma go cell lines.

$Ras^{V12}$ MEFs were also transduced with PRAME or RARα retrovirus and treated with 1 µM PXD101 for 16 hrs. Extracts were immunoblotted for acetyl-H3, p21, PRAME, RARα and CDK4 (control). It was found that expression of PRAM or RARα in $RAs^{V12}$-MEFs did not prevent the increase in histone H3 acetylation nor the well-documented induction of $p21^{c1P1}$ expression by HDACi-treatment (Richon et al 2000), suggesting that PRAME and RARα act downstream of HDACs to suppress the effects of the HDACi on cell proliferation.

PRAME was first identified as an antigen in human melanoma that triggers cytotoxic T cell-mediated anti tumour immune responses (Ikeda et al 1997). PRAME is also overexpressed in a variety of other human malignancies, including acute and chronic leukemias, non-small-cell lung carcinoma, head and neck cancer, renal carcinoma, and its expression is prognostic for a poor clinical is outcome in breast cancer (Ikeda et al 1997; van It Veer et al, 2002; van Hazen et al, 1998; Nemann et al, 1998, Boon et al, 2003). However, no function for PRAME has been described to date. Since HDAC inhibitors affect gene transcription, we asked if PRAME acts as a repressor or activator of transcription. To test this, we co-transfected a vector in which PRAME is fused to the DNA binding domain of the yeast transcription factor GAL4 (GAL4-PRAME) with a GAL4-luciferase reporter plasmid in human 293 cells. FIG. 1a shows that expression of GAL4-PRAME caused a strong and dose-dependent inhibition of gene expression, suggesting that PRAME is a repressor of transcription. Treatment of cells with HDACi did not affect this, indicating that PRAME repression is mostly HDAC-independent (FIG. 1b).

Figure 4:
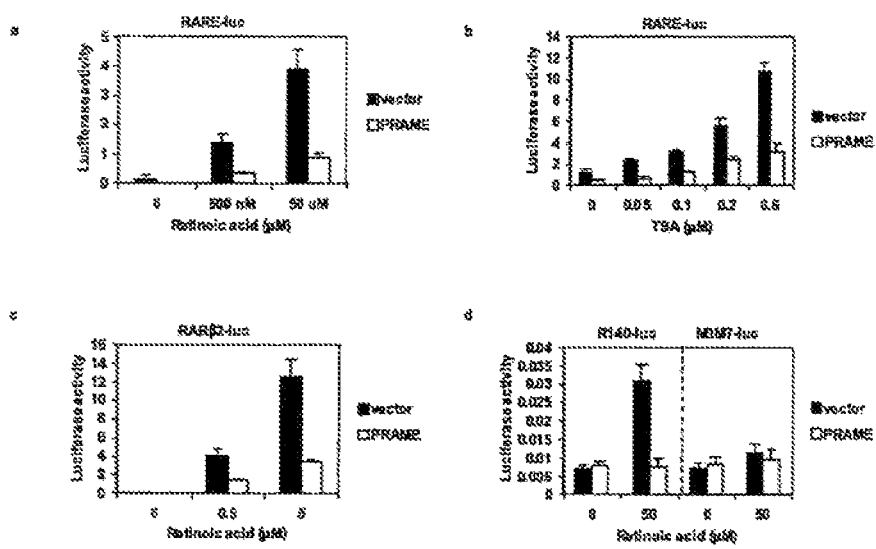
FIG. 4: PRAME represses RAR signalling. a, B16 melanoma cells were transfected with RARE-luciferase and either PRAME or empty vector and treated with RA. b, Ras $^{V12}$ MEFs were transfected as in a, and treated with TSA. c, B16 melanoma cells were transfected with a RARβ2-promoter luciferase reporter (RARβ2-luc) and either PRAME or empty vector and treated with RA. d, Ras $^{V12}$ MEFs were transfected with a RARβ2-luciferase reporter (R140-luc) or a RARβ2-luciferase reporter with a mutated RARE (M3M7-luc) and either PRAME or empty vector and treated with RA. Average values are of three independent transfections (±s.d.).

Because we identified both PRAME and RARα in the genetic screen described above, we asked if these two proteins act in the same pathway. To address this, we asked if PRAME affects RAR signalling. We transfected PRAME into RAS$^{V12}$-MEFs together with a reporter gene driven by a Retinoic Acid Responsive Element (RARE-luciferase). FIG. 1c shows that PRAME expression strongly inhibited RA-induced activation of the RA-responsive reporter gene over a wide range of RA concentrations. Similar results were obtained in mouse B16 melanoma cells (FIG. 4). PRAME also repressed RAR signalling induced by HDACi treatment (FIG. 1d and FIG. 4). Importantly, ectopic expression of RARα also repressed the activation of the RA-responsive reporter gene construct by HDACi (FIG. 1e). Thus, both cDNAs that we identified in the genetic screen described above suppress HDACi-mediated activation of the RA-responsive reporter gene. This raises the possibility that suppression of HDACi-induced RA-signalling (Lin et al 1998, and FIG. 1c) is one way in which cells can become resistant to HDACi treatment. However, our data do not exclude that RARα and PRAME act on other pathways to mediate escape from HDACi-induced growth arrest.

To further address the effect of PRAME on RA-signalling we studied RARβ, as this gene contains a RA-responsive element in its promoter (de The et al 1990). To ask if PRAME expression affected the expression of the endogenous RARβ gene, F9 mouse embryo carcinoma cells were transfected with PRAME or empty vector, treated with $10^{-7}$ M RA, and immunoblotted for RARβ. Average values of three independent transfections were determined. It was found that endogenous RARβ protein expression was induced only in parental and mock-transfected F9 cells, but not in PRAME-transfected F9 derivatives. PRAME also repressed RA-induced activation of a RARβ2 promoter-luciferase construct in both RAS$^{V12}$-MEFs and B16 melanoma cells (FIG. 4). Together, these data indicate that PRAME is a negative regulator of RA-signalling.

The observed effect of PRAME on RAR signalling could result from a physical interaction of PRAME with RAR or from more indirect effects. To ask if PRAME physically interacts with RAR, we stably expressed a TAP-tagged (Rigaut et al, 1999) PRAME in RAS$^{V12}$-MEFs. Ras$^{V12}$ MEFs were infected with TAP-PRAME, RARα, or GFP (control) retrovirus and cultured in the presence of 1 μM PXD101. TAP-PRAME was functional as it rescued cells from PXD101-induced growth arrest.

Ras$^{V12}$ MEFs (MEF) were transduced with TAP-tagged PRAME and expression levels were compared to endogenous PRAME in SK23 and A375 melanoma. Importantly, TAP-PRAME protein levels were comparable to the levels of endogenous PRAME in the human melanoma cell lines SK23 and A375.

TAP-PRAME was immunoprecipitated (using IgG beads (Rigaut et al, 1999), indicated as anti-TAP) before and after treatment with 1 μM RA and precipitates were immunoblotted for RARα. It was found that endogenous RARα co-precipitates with TAP-PRAME, both in the absence and presence of RA, indicating that PRAME and RARα form a ligand-independent complex at protein concentrations seen in human tumours.

Figure 2:
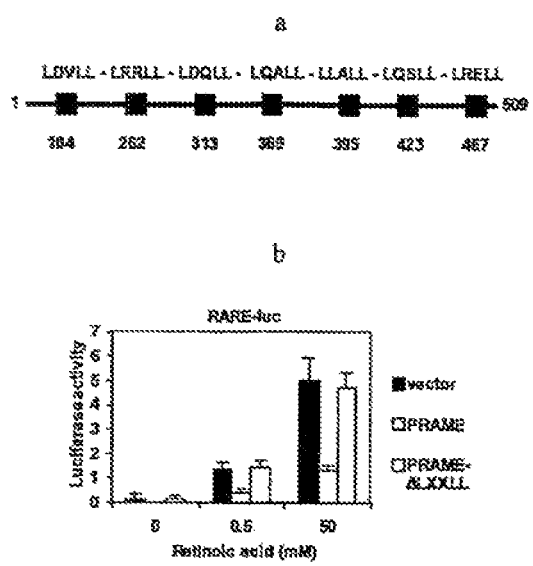
FIG. 2: PRAME and its interaction with RAR. a, Schematic representation of PRAME. Amino acid residue numbers of the seven NR box motifs are indicated. b, B16 melanoma cells were transfected with RARE-luc and either PRAME or PRAME-ΔLXXLL, and treated with RA. Average values are of three independent transfections (±s.d.).

The amino-acid sequence of PRAME contains seven potential leucine-rich nuclear receptor (NR) boxes (LXXLL motifs (Heery et al, 1997), FIG. 2c). Many modulators of nuclear receptor activity interact directly with their target receptors via one or more of these motifs (Heery et al, 1997; Torchia et al, 1997). To test if these motifs in PRAME are required for inhibition of RAR signalling, we introduced point mutations in PRAME, to change several of the leucine residues in each of the seven NR boxes into valines. The resulting mutant, PRAME-ΔLXXLL, was expressed at comparable levels as wild type PRAME (as determined by immunoblotting), but failed to repress RAR signalling (FIG. 2b). The mutant did not bind RARα, when immunoprecipitations as described above were performed. We conclude that the LXXLL motifs in PRAME are required for modulation of RAR activity.

RA induces proliferation arrest, differentiation and apoptosis in many cell types. We therefore asked if PRAME expression affected the RA-induced differentiation of F9 mouse embryo carcinoma cells towards parietal endoderm (Strickland and Mandavi, 1978). F9 cells were stably transfected with PRAME or control vector and individual colonies were selected. In the to absence of RA, the morphology of all transfected cells was the some as that of parental F9 cells. However, F9 cells stably transfected with PRAME or empty vector and treated with $10^{-7}$ M RA were resistant to RA-induced morphological differentiation and growth arrest. Apart from differentiating, a fraction of F9 cells treated with RA dies by apoptosis (Atencia et al, 1994). PRAME expression in F9 cells also conferred resistance to RA-induced apoptosis as cleaved caspase 3 was apparent in vector controls, but not in PRAME transfectants. We conclude that PRAME expression confers resistance to RA-induced proliferation arrest, differentiation and apoptosis.

Human melanoma cells often have defects in RA signalling (Atencia et al, 1994; van der Leede et al, 1993). As PRAME is over-expressed in some 90% of melanomas (Ikeda et al, 1997), we asked if PRAME expression explained their RA-unresponsiveness. To test this, we inhibited PRAME expression in several RA-resistant melanoma cell lines (Demary et al, 2001) through RNA interference. We selected a unique 21-mer sequence in the PRAME transcript for cloning into pRETRO-SUPER (pRS), a vector that mediates suppression of gene expression through synthesis of short hairpin RNAs having small interfering RNA (siRNA)-like properties (Brummelkamp et al, 2002a; Brummelkamp et al 2002b). 293 cells were transfected with flag-tagged PRAME and pRS-PRAME or pRS empty vector. Extracts were immunoblotted for flag or GFP (control). In addition, A375 cells were transfected with RARE-luciferase and either pRS-PRAME or empty vector and treated with RA. Average values of three independent transfections were determined. A375-PRAME$^{KD}$ cells and control A375 cells were immunoblotted for PRAME, RARα, p21, and RARβ.

Figure 5:
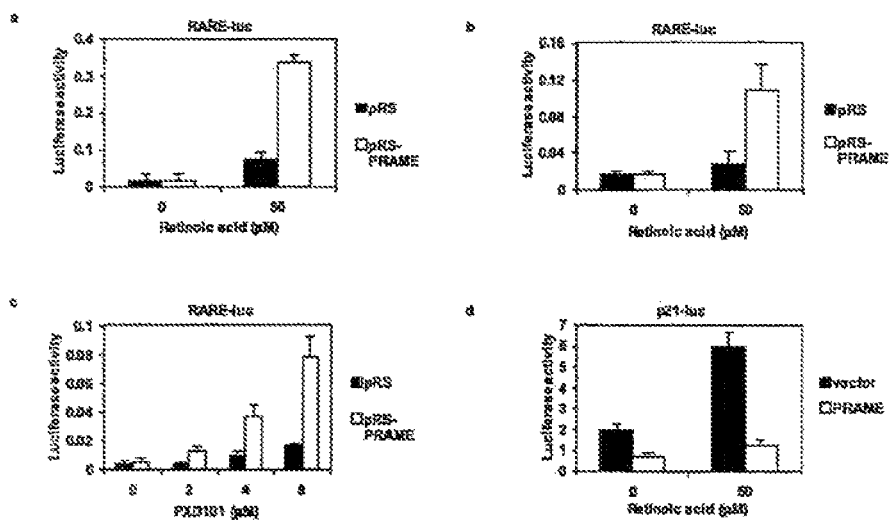
FIG. 5: Effects of PRAM expression on RA-signalling in melanoma. a, b, FM6 (a) and SK23 (b) human melanoma cells were transfected with RARE-luciferase and either pRS-PRAME or empty vector and treated with RA. o, A375 cells were transfected as in a, and treated with PXD101. d, 816 melanoma cells were transfected with a p21-promoter luciferase construct and either PRAME or empty vector and treated with RA. Average values are of three independent transfections (±s.d.).

It was found that pRS-PRAME mediates effective decrease of ectopically expressed PRAME as well as endogenous PRAME protein. To ask if knockdown of PRAME restores RA-responsiveness, we co-w transfected A375 human melanoma cells, which express high levels of endogenous PRAME, with pRS-PRAME and a RA-responsive reporter gene construct. The PRAME knockdown greatly enhanced RA-signalling in the A375 cells as determined by using the RARE-luciferase construct. Similar results were found in the SK23 and FM6 human melanoma cell lines (FIG. 5). Melanomas are relatively resistant to treatment with HDACi (Plumb et al, 2003), but A375 cells transfected with pRS-PRAME had enhanced PXD101-induced RAR signalling compared to vector controls (FIG. 5).

Figure 3:
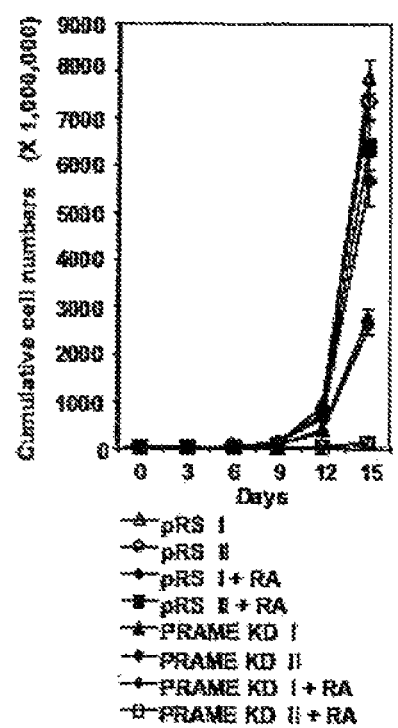
FIG. 3: Effects of PRAME expression. Proliferation curve of A375-PRAME$^{KD}$ cells grown in normal medium or medium supplemented with 5 μM RA.

To assess the effect of PRAME knockdown on cell proliferation, we generated stable derivatives of A375 melanoma having shRNA-mediated knockdown of PRAME expression (A375-PRAME$^{KD}$). These A375-PRAME$^{KD}$ cells were cultured for 15 days according to the 3T3 protocol. FIG. 3 shows that PRAME$^{KD}$ significantly decreased proliferation rates, especially when cultured in the presence of RA. Consistent with the notion that PRAME$^{KD}$ restores RA signalling, we found that the known RA target genes RARβ and p21$^{C1P1}$ (de The et al, 1990, Liu et al 1996) were significantly up-regulated in PRAME$^{KD}$ cells, and their induction was further go enhanced by 5 µM RA treatment. Consistent with this, a p21 promoter-luciferase reporter was activated by RA in B16 melanoma cells, but its activity was strongly suppressed by PRAME (FIG. 5). RARα is degraded by the proteasome in response to RA signalling (zhu et al, 1999) and in agreement with this, RARα protein levels were significantly decreased in PRAME$^{KD}$ cells. Together, these data indicate that PRAME is a major regulator of RA-signalling, which contributes to RA-unresponsiveness of human melanomas.

The presence of NR boxes in PRAME (FIG. 2a) suggests that the interaction between PRAME and RARα takes place via one or more or more of these motifs. To test if the NR boxes of PRAME are required for binding to RAR and inhibition of RAR signaling, le point mutations were introduced in each of the seven LXXLL motifs in PRAME by changing conserved leucine (L) residues into valines (V). The resulting PRAME mutants were named after the respective NR boxes that were mutated. One additional mutant was made in which all seven LXXLL motifs were mutated, referred to is as PRAME-ΔLXXLL. MEFs were transfected with RARE-luc and PRAME or PRAME NR box mutants and treated with RA.

Six out of seven PRAME single NR box mutants inhibited RAR signaling to a similar extent as wild-type PRAME except for the box 7 PRAME-LREVV mutant. This mutant was as defective in repressing RAR signaling as the PRAME mutant in which all 7 NR boxes were mutated. Consistent with this observation, endogenous RARα failed to co-immunoprecipitate with a TAP-PRAME-LREVV mutant protein. To investigate if the repression function of PRAME was affected by the LREVV mutation, we tested the effect of cotransfection of a Gal4-PRAME-LREVV fusion protein on expression of the Gal4-luciferase reporter. Gal4-PRAME-LREVV inhibited expression to a similar extent as Gal4-PRAME, indicating that repression was not affected.

A mammalian two-hybrid assay was performed in which a wild-type PRAME construct, Gal4-PRAME-LRELL (416-509) or the box 7 mutant Gal4-PRAMELREVV (416-509) was co-expressed with VP16-RARα LBO in the presence of RA. Normalized luciferase activities were determined as the average of three independent transfections. The PRAME wildtype LRELL NR box interacted with VP16-RARα, but introduction of the LREVV mutation in PRAME disrupted the association. Taken together, these data suggest that an intact LRELL motif in PRAME is required for binding to RARα, and repression of RAR signaling.

Human melanomas often have defects in RAR signaling (Demary et al., 2001; van der Leede et al., 1993) and PRAME is over-expressed in 88% of primary melanomas and 95% of melanoma metastases (Ikeda et al., 1997). This raises the possibility that PRAME expression is responsible for their RA-unresponsiveness. To test this hypothesis, we inhibited PRAME expression in three different melanoma cell lines (A375, FM6 and SK23) through stable RNA interference (Brummelkamp et al., 2002a). Transfection of A375 human melanoma cells with a PRAME-specific shRNA vector (pRS-PRAME) caused a significant decrease in levels of endogenous PRAME. Knockdown of PRAME greatly enhanced RAR signaling in three human melanoma cell lines that are relatively insensitive to RA. Together, these data support the notion that PRAME expression confers cellular resistance to RA in human melanoma.

To examine the role of PRAME in RA-responsiveness in vivo, we used a human melanoma xenograft model. Nude mice were subcutaneously transplanted with parental A375 into one flank and A375-PRAMEKD cells in the opposite flank and the mice were treated p.o. daily with either 5 mg/kg RA or vehicle only, while tumor volumes were measured weekly. Tumor growth was severely retarded by RA treatment in PRAMEKD melanomas, but not in parental A375 melanomas that grew in a different anatomical location in the same mice. Together, these data suggest that PRAME functions as a negative regulator of RAR signaling, which contributes to RA-unresponsiveness of human melanomas.

The data presented here indicate that PRAME is a dominant, ligand-independent, repressor of RAR signalling, resulting in a decreased cellular response to RA-driven differentiation, growth arrest and/or apoptosis. PRAME is distinct from the known co-repressors of nuclear receptors such as N-CoR and SMRT, whose interaction with nuclear receptors is lost upon ligand binding (Xu et al 1999). Our data also identify PRAME expression as a novel mechanism by which tumour cells can escape tumour-suppressive RA signalling. In this respect, PRAME expression phenocopies the PML-RARα and PLZF-RARα translocations seen in acute promyelocytic leukemia. Hence, melanoma cells and other tumour cells that over-express PRAME have a selective advantage over PRAME-negative cells, which may explain why PRAME expression is retained by tumour cells in vivo, despite the fact that its presence elicits a cytotoxic T cell-mediated anti-tumour immune response (Ikeda et al., 1997). Finally, our data suggest a strategy to select subjects that are likely to benefit most from treatment with HDACi compounds.

Methods.

Reagents, Antibodies and Plasmid Construction

Full-length PRAME in pcDNA3.1/Neo(+) was a gift from Drs. M. Griffioen and C. Melief (Leiden, The Netherlands). Retroviral PRAME was generated by cloning a BamHI-XhoI PRAME fragment into pMX-IRES-GFP (pMIG). TAP-tagged PRAME was generated by cloning a PCR amplified EcoRI PRAME fragment into pZOME-1-N (Cellzome) and Gal4-PRAME was generated by cloning a BamHI-XbaI PRAME fragment into a GAL4-DBD expression vector. Retroviral RARα was generated by cloning an EcoRI digested RARα cDNA into pMX. The PRAME-ΔLXXLL mutant was made using the QuikChange Site-Mutagenesis kit (Stratagene). PRAME-ΔLXXLL has multiple of the leucines (L) in the LXXLL motifs changed into valines (V). The resulting sequences were: LDVVV, VRRLL, LDQVV, VQALL, LLAVV, LDQVV, LREVV.

pRS-PRAME was generated by ligating synthetic oligos against the target sequence GGTGCCTGTGATGAAT-TGTTC (SEQ ID NO:2) into pRS in a manner similar to that described previously (Brummelkamp et al, 2002a). The following oligonucleotide sequences were annealed:

```
                                                                                      (SEQ ID NO: 3)
5'-GATCCCCGGTGCCTGTGATGAATTGTTCTTCAAGAGAGAACAATTCATCACAGGCACCTTTTTGGAAA-3'
and
                                                                                      (SEQ ID NO: 4)
5'-AGCTTTTCCAAAAAGGTGCCTGTGATGAATTGTTC TCTCTTGAAGAACAATTCATCACAGGCACCGGG-3'
``` to provide a double strand with overhanging BamH1 ends. This was ligated into the vector. Expression from the H1-RNA promoter provides a transcript commencing at start of the target sequence (5' underlined region in SEQ ID NO:3), through a hairpin loop (italics in SEQ ID NO:3 above), and terminating at the end of the complement (3' underlined region of SEQ ID NO:3) of the target sequence, with the addition of a 2 nt overhang.

RA-responsive luciferase constructs and RARα cDNA were kindly provided by Dr. H, Stunnenberg (Nijmegen, The Netherlands). The erythroleukemia retroviral cDNA library was provided by Dr. Koh and Dr. Daley (Cambridge, Mass.). All-trans-retinoic acid (ATRA) and TSA were from SIGMA, and PXD101 was provided by Topotarget/Prolifix Ltd (Abingdon, UK). Anti-PRAME affinity-purified antibodies were a generous gift from Dr. P. Coulie (Brussels, Belgium) and were generated by immunizing rabbits with peptides FPEP-EAAQPMTKKRKVDG (AH-151; SEQ ID NO:6) and CGDRTFYDPEPIL (AH-152; SEQ ID NO:7). Antibodies against RARα (C-20), RARβ (C-19), p21 (F5), GFP (FL), CDK4 (C-22), and CDK2 (H-298) were from Santa Cruz Biotechnologies, anti-acetyl H3 was from Serotec, anti-Ras (R02120) was from Transduction laboratories, and anti-cleaved caspase-3 (Asp 175) was from Cell Signaling.

Cell Cultures, Genetic Screen, and Colony Formation Assays

All cells were cultured in DMEM supplemented with 10% fetal calf serum (FCS). *Phoenix* packaging cells were used to generate ecotropic retroviruses as described (Serrano et al, 1997). p53$^{-/-}$ MEFs were infected with pBabe-Puro-RAS$^{V12}$ retrovirus and selected for puromycin resistance. The resulting RAS$^{V12}$-MEFs were infected with library retroviral supernatants and re-plated at a cell density of 5·10$^4$ cells/10 cm dish 48 hrs after infection. HDAC inhibitor PXD101 (1 µM) or TSA (0.1 µM) was added to the medium 16 hours after reseeding and the medium with HDAC inhibitor was refreshed every third day.

Transfections and Reporter Assays

Transfections were carried out using the Lipofectamine reagent (Invitrogen), except for Ras$^{V12}$ MEFs and *Phoenix* cells, which were transfected using calcium phosphate precipitation. RA-based reporter assays were done in DMEM with charcoal-stripped FCS (Hyclone). In reporter assays 0.5 µg of reporter-luciferase, 1 ng CMV-renilla, and 3 µg of the indicated DNA were transfected. RA, PXD101, or TSA was added 24 hrs after transfection and assays were performed 48 hrs after transfection. In knock-down experiments, RA or PXD101 was added 72 hrs after transfection and assays were performed 96 hrs after transfection. Luciferase activities shown represent ratios between luciferase and renilla internal control values.

Western Blotting and Co-Immunoprecipitation

Cells were lysed in Ripa buffer (50 mM Tris pH 8.0, 150 mM NaCl, 1% NP-40, 0.5% deoxycholic acid, and 0.1% SDS) supplemented with protease inhibitors (Complete; Roche) and 0.2 nM PMSF and proteins were separated on 10-14% SDS-PAGE gels. Proteins were transferred to polyvinylidine difluoride membranes (Immobilon P, Millipore) and Western blots were probed with the indicated antibodies. For TAP (co-)immunoprecipitations cells were lysed in ELB buffer (0.25 M NaCl, 0.1% NP-40, 50 mM HEPES pH 7.3) supplemented with protease inhibitors and PMSF. Lysates were incubated with IgG-coated sepharose beads (Amersham) to immunoprecipitate TAP and TAP-PRAME (Rigaut et al 1999), indicated as anti-TAP, or with protein A beads and normal mouse serum (mock IP) for 2 hrs, washed, and separated on SDS-PAGE gels.

Differentiation and Proliferation Assays

F9 cells were stably transfected with PRAME or empty vector and resistant cells were differentiated in 10$^{-7}$ M RA for 5 days. A375 cells were stably transfected with pRS-PRAME or empty vector and stable clones were cultured according to the 3T3 protocol. Medium with RA was refreshed every 24-48 hrs.

Mouse Tumor Xenografts

Female 5-6 week old athymic BALB-C nude mice (nu/nu) were s.c. implanted with 1×10$^6$ cells bilaterally into the axial regions. Each mouse received A375-PRAMEKD cells in its right flank and control A375 cells in its left flank. Mice were randomized into treatment groups and treated with 5 mg/kg RA or vehicle (ethanol in sunflower oil) p.o. with a 20-gauge intragastric feeding tube daily. Tumor diameter was measured with calipers weekly. The pRS vector which was used to generate A375-PRAMEKD cells is a self-inactivating retroviral vector, to prevent re-activation and spreading of virus (Brummelkamp et al., 2002a; Brummelkamp et al., 2002b). The experiment was performed twice, with n=20 and n=10 mice and results were similar in both experiments.

References

Altucci, L. & Gronemeyer, H. The promise of retinoids to fight against cancer. Nat Rev Cancer 1, 181-93. (2001).

Atencia, R., Garcia-Sanz, M., Unda, F. & Arechaga, J. Apoptosis during retinoic acid-induced differentiation of F9 embryonal carcinoma cells. Exp Cell Res 214, 663-7. (1994).

Boon, K. et al. Comparison of medulloblastoma and normal neural transcriptomes identifies a restricted set of activated genes. Oncogene 22, 7687-94. (2003).

Brehm A. et al Retinoblastoma protein recruits histone deacetylase to repress transcription Nature 391, 597-601 (1998)

Brummelkamp, T. R., Bernards, R. & Agami, R. A System for Stable Expression of Short Interfering RNAs in Mammalian Cells. Science 296, 550-553. (2002a).

Brummelkamp, T., Bernards, R. & Agami, R. Stable suppression of tumorigenicity by virus-mediated RNA interference. Cancer Cell 2, 243-247 (2002b).

David G. et al Histone deacetylase associated with mSin3A mediates repression by the acute promyelocytic leukemia associated PLZF protein. Oncogene 16(19), 2549-2556 (1998)

Davie J. R. Covalent modifications of histones: expression from chromatin templates Curr. Opin. Genet. Dev. 8 173-178 (1998)

de The, H., Vivanco-Ruiz, M. M., Tiollais, P., Stunnenberg, H. & Dejean, A. Identification of a retinoic acid responsive element in the retinoic acid receptor beta gene. Nature 343, 177-80. (1990).

Demary, K., Wong, L. & Spanjaard, R. A. Effects of retinoic acid and sodium butyrate on gene expression, histone acetylation and inhibition of proliferation of melanoma cells. Cancer Lett 163, 103-7. (2001).

Desai D. et al. Chemopreventive efficacy of suberanilohydroxamic acid (SAHA), a cytodifferentiating agent, against tobacco-specific nitrosaminer 4-(-methylnitrosamino)-1-(3-pyridyl)-1-butanone (NNK)-induced lung tumorigenesis in female A/J mice Proc. AACR 40, abstract #2396. (1999)

Emiliani S. et al Characterisation of a human RPD3 homolog, HDAC3 Proc Natl. Acad. Sci. USA, 95, 2795-2800 (1998)

Finnin et al Structures of a histone deacetylase homologue bound to the TSA and SAHA inhibitors Nature 401, 188-193 (1999)

Freemantle, S. J., Spinella, M. J. & Dmitrovsky, E. Retinoids in cancer therapy and chemoprevention: promise meets resistance. Oncogene 22, 7305-15. (2003).

Grozinger et al Three proteins define a class of human histone deacetylases related to Hdalp Proc. Natl. Acad. Sci. USA 96, 4868-4873 (1999)

Heery, D. M., Kalkhoven, E., Hoare, S. & Parker, M. G. A signature motif in transcriptional co-activators mediates binding to nuclear receptors. Nature 387, 733-736 (1997).

Howe L. et al histone acetyltransferase complexes and their link to transcription Crit. Rev. Eukaryot. Gene Expr. 9(3-4) 231-243

Ikeda, H. et al. Characterization of an antigen that is recognized on a melanoma showing partial HLA loss by CTL expressing an NK inhibitory receptor. Immunity 6, 199-208. (1997).

Jacobs, J. J. et al. Senescence bypass screen identifies TBX2, which represses cdkn2a (p19ARF) and is amplified in a subset of human breast cancers. Nat Genet. 26, 291-299. (2000).

Johnstone, R. W. Histone-deacetylase inhibitors: novel drugs for the treatment of cancer. Nat Rev Drug Discov 1, 287-99. (2002).

Kao et al Isolation of a novel histone deacetylase reveals that class I and class II dseacetylases promote SMRT-mediated repression Genes Dev. 14, 55-66 (2000)

Kijima et al trapoxin an antitumor cyclic tetrapeptide, is anirreversible inhibitor of mammalian histone deacetylase J. Biol. Chem. 268, 22429-22435 (1993).

Kim et al Oxamfiatin is a novel antitumor compound that inhibits mammalian histone deacetylase Oncogene 18 (15), 2461-2470. (1999).

Kitamura K et al Histone deacetylase inhibitor but not arsenic trioxide differentiates acute promyelocytic leukemic cells with t(11;17) in combination with all-trans retinoic acid. Br. J. Haematol. 108(4), 696-702 (2000)

Kouzarides, T. Histone acetylases and deacetylases in cell proliferation. Curr., Opin. Genet. Dev 9(1) 44-48 (1999)

Kuo, M. H. & Allis, C. D. Roles of histone acetyltransferases and deacetylases in gene regulation. Bioassays 20, 615-26. (1998).

Kwon et al Depudecin induces morphological reversion of transformed fibroblasts via the inhibition of histone deacetylase Proc. Natl. Acad. Sci. USA 95, 3356-3361.

Laherty C. D et al Histone deacetylases associated with the mSin3 corepressor mediate mad transcriptional repression Cell 89(3), 349-356 (1997)

Lea et al Increased acetylation of histones induced by diallyl disulfide and structurally related molecules. Int. J. Oncol. 2, 347-352.

Lea M. A. and Tulsyan N. Discordant effects of butyrate analogues on eryhtroleukemia cell proliferation, differentiation and histone deactylase. Anticancer Res. 15(3), 879-883 (1995)

Lin, R. J. at al. Role of the histone deacetylase complex in acute promyelocytic leukaemia. Nature 391, 811-814. (1998).

Liu, M., Iavarone, A. & Freedman, L. P. Transcriptional activation of the human p21(WAF1/CIP1) gene by retinoic acid receptor. Correlation with retinoid induction of U937 cell differentiation. J Biol Chem 271, 31723-8. (1996).

Marks, P. et al. Histone deacetylases and cancer: causes and therapies. Nat Rev Cancer 1, 194-202. (2001).

Nakajima et al FR901288, a potent antitumor antibiotic, is a novel histone deacetylase inhibitor. Exp. Cell Res. 241, 126-133 (1998)

Narlikar, G. J., Fan, H. Y. & Kingston, R. E. Cooperation between complexes that regulate chromatin structure and transcription. Cell 108, 475-87. (2002).

Neumann, E. et al. Heterogeneous expression of the tumor-associated antigens RAGE-1, PRAME, and glycoprotein 75 in human renal cell carcinoma: candidates for T-cell-based immunotherapies? Cancer Res 58, 4090-5. (1998).

Ng H. H. and Bird A. histone deacetylases: silencers for hire Trends Biochem Sci. 25(3) 121-126

Pazin M. J. et al What's up and down with histone deacetylarion and transcription? Cell 89(3) 325-328

Plumb, J. A. et al. Pharmacodynamic response and inhibition of growth of human tumor xenografts by the novel histone deacetylase inhibitor PXD101. Mol Cancer Ther 2, 721-8. (2003).

Richon et al Second generation hybrid polar compounds are potent inducers of transformed cell differentiation Proc. Natl. Acad. Sci. USA 93, 5705-5708 (1996).

Richon V et al A class of hybrid polar inducers of transformed cell differentiation inhibits histone deacetylases Proc. Natl. Acad. Sci. USA 95, 3003-3007 (1998)

Richon, V. M., Sandhoff, T. W., Rifkind, R. A. & Marks, P. A. Histone deacetylase inhibitor selectively induces p21WAF1 expression and gene-associated histone acetylation. Proc Natl Acad Sci USA 97, 10014-9. (2000).

Rigaut, G. et al. A generic protein purification method for protein complex characterization and proteome exploration. Nat Biotechnol 17, 1030-2. (1999).

Saito et al. A synthetic inhibitor of histone deacetylase MS-27-275, with marked in in vivo antitumor activity against human tumors. Proc. Natl. Acad. Sci. USA 96, 4592-4597 (1999)

Serrano, M., Lin, A. W., McCurrach, M. E., Beach, D. & Lowe, S. W. Oncogenic ras provokes premature cell senescence associated with accumulation of p53 and p16INK4a. Cell 88, 593-602 (1997).

Sonoda et al. Oxamflatin: a novel compound which reverses malignant phenotype to normal one via induction of JunD. Oncogene 13, 143-149 (1996)

Strickland S et al Structure-activity relationships of a new series of retinoidal benzoic acid derivatives as measured by induction of differentiation of murine F9 teratocarcinoma cells and human HL-60 promyelocytic leukemia cells. Cancer Res 43(11) 5268-72. (1983)

Strickland, S. & Mandavi, V. The induction of differentiation in teratocarcinoma stem cells by retinoic acid. Cell 15, 393-403 (1978).

Suzuki et al. Synthesis and histone deacetylase inhibitory activity of new benzamide derivatives J. Med. Chem. 42, 3001-3003 (1999)

Taunton J. et al A mammalian histone deacetylase related to the yeast transcriptional regulator Rpd3p Sciencde 272 408-411 (1996)

Torchia, J. et al. The transcriptional co-activator p/CIP binds CBP and mediates nuclear-receptor function. Nature 387, 677-684 (1997).

Ueda H. et al FR901228, a nove31 antitumor bicyclic depsipeptide produced by *Chromobacterium violaceum* No. 968.111. Antitumor activities on experimental tumors in mice J. Antibiot. (Tokyo) 47 (3), 315-323 (1994).

van't Veer, L. J. et al. Gene expression profiling predicts clinical outcome of breast cancer. Nature 415, 530-536 (2002).

van Baren, N. at al. PRAME, a gene encoding an antigen recognized on a human melanoma by cytolytic T cells, is expressed in acute letikaemia cells. Br J Haematol 102, 1376-9. (1998).

Van den Wyngaert et al Cloning and characterization of human histone deacetylase 8 FEBS Lett. 478, 77-83 (2001)

van der Leede, B. M., van den Brink, C. E. & van der Saag, P. T. Retinoic acid receptor and retinoid X receptor expression in retinoic acid-resistant human tumor cell lines. Mol Carcinog 8, 112-22. (1993).

Verma A. K. et al. Inhibition of 12-O-tetradecanoylphorbol-13-acetate-induced ornithine deacarboxylase activity in mouse epidermis by vitamin A analogs (retinoids. Cancer Res. 38(3) 793-801 (1978)

Warrell R. P. et al Therapeutic targeting of transcription in acute promyelocytic leukemia by use of an inhibitor of histone deacetylase. J. Natl. Cancer Inst. 90(21) 1621-1625. (1998)

Watkins, C., et al., 2002, "Carbamic acid compounds comprising a sulfonamide linkage as HDAC inhibitors," published international (PCT) patent application number WO 02/30879 (PCT/GB01/04326) published 18 Apr. 2002

Watkins, C., et al., 2002, "Carbamic acid compounds comprising an ether linkage as HDAC inhibitors," published international (PCT) patent application number WO 02/26703 (PCT/GB01/04327) published 4 Apr. 2002

Watkins, C., et al., 2002, "Carbamic acid compounds comprising an amide linkage as HDAC inhibitors," published international (PCT) patent application number WO 02/26696 (PCT/GB01/04329) published 4 Apr. 2002

Watkins, C., et al., 2003, "Carbamic acid compounds comprising a piperazine linkage as HDAC inhibitors," published international (PCT) patent application number WO03/082288 (PCT/GB03/01463) published 9 Oct. 2003.

Wong J. et al Distinct requirements for chrmatin assembly intranscriptional repression by thyroid hormone receptor and histone deacetylase EMBO J. 17(2), 520-534 (1998)

Xu, L., Glass, C. K. & Rosenfeld, M. G. Coactivator and corepressor complexes in nuclear receptor function. Curr Opin Genet Dev 9, 140-7. (1999).

Yang W. M. et al Isolation and characterization of cDNAs corresponding to an additional member of the human histone deacetylase family J. Biol. Chem. 272, 28001-28007 (1997)

Yang W. M. et al Transcriptional repression of YY1 is mediated by interaction of a mammalioan homolog of the yeast global regulator RPD3 Proc. Natl. Acad. Sci. USA 93, 12845-12850 (1996)

Yoshida and Beppu Reversible arrest of proliferation of rat 3Y1 fibroblasts in both G1 and G2 phases by trichostatin A. Exp. Cell Res. 177, 122-131. (1988)

Yoshida and Horinouchi, Trichostatin A and leptomycin: inhibition of histone deacetylation and signal dependent nuclear export Ann. N.Y. Acad. Sci. 886, 23-26 (1999)

Yoshida et al Trichostatin A and trapoxin: novel chemical probes for the role of histone acetylation in chromatin structure and function Bioassays 17, 423-430. (1995)

Yoshida M. et al Potent and specific inhibition of mammalian histone deacetylase both in vivo and in vitro by trichostatin A J. Biol. Chem. 265(28), 17174-17179 (1990)

Yoshida M. et al Structural specificity for biological activity of trichostatin A, a specific inhibitor of mammalian cell cycle with potent differentiation inducing activity in Friend leukemia cells J. Antibiot. (Tokyo) 43(9), 1101-1106 (1990)

Zhu, J. et al. Retinoic acid induces proteasome-dependent degradation of retinoic acid receptor alpha (RARalpha) and oncogenic RARalpha fusion proteins. Proc Natl Acad Sci U S A 96, 14807-12. (1999).

```
SEQ ID NO: 1-Human PRAME
    1 gggaaaccga ctcctgggag cagggaggaa cgcgcgctcc agagacaact tcgcggtgtg 61 gtgaactctc tgaggaaaaa cacgtgcgtg gcaacaagtg actgagacct agaaatccaa 121 gcgttggagg tcctgaggcc agcctaagtc gcttcaaaat ggaacgaagg cgtttgtggg 181 gttccattca gagccgatac atcagcatga gtgtgtggac aagcccacgg agacttgtgg 241 agctggcagg gcagagcctg ctgaaggatg aggccctggc cattgccgcc ctggagttgc 301 tgcccaggga gctcttcccg ccactcttca tggcagcctt tgacgggaga cacagccaga 361 ccctgaaggc aatggtgcag gcctggccct tcacctgcct ccctctggga gtgctgatga 421 agggacaaca tcttcacctg gagaccttca aagctgtgct tgatggactt gatgtgctcc 481 ttgcccagga ggttcgcccc aggaggtgga aacttcaagt gctsgattta cggaagaact 541 ctcatcagga cttctggact gtatggtctg gaaacagggc cagtctgtac tcatttccag 601 agccagaagc agctcasccc atgacaaaga agcgaaaagt agatggtttg agcacagagg 661 cagagcagcc cttcattcca gtagaggtgc tcgtagacct gttcctcaag gaaggtgcct 721 gtgatgaatt gttctcctac ctcattgaga aagtgaagcg aaagaaaaat gtactacgcc 781 tgtgctgtaa gaagctgaag attttttgcaa tgcccatgca ggatatcaag atgatcctga
```

```
 841 aaatggtgca gctggactct attgaagatt tggaagtgac ttgtacctgg aagctaccca 901 ccttggcgaa attttctcct tacctgggcc agatgattaa tctgcgtaga ctcctcctct 961 cccacatcca tgcatcttcc tacatttccc cggagaagga agagcagtat atcgcccagt 1021 tcacctctca gttcctcagt ctgcagtgcc tgcaggctct ctatgtggac tctttatttt 1081 tccttagagg ccgcctggat cagttgctca ggcacgtgat gaacccttg gaaaccctct 1141 caataactaa ctgccggctt cggaaggggg atgtgatgca tctgtcccag gtcccagcg 1201 tcagtcagct aagtgtcctg agtctaagtg gggtcatgct gaccgatgta agtcccgagc 1261 ccctccaagc tctgctggag agagcctctg ccaccctcca ggacctggtc tttgatgagt 1321 gtgggatcac ggatgatcag ctccttgccc tcctgccttc cctgagccac tgctcccagc 1381 ttacaacctt aagcttctac gggaattcca tctccatatc tgccttgcag agtctcctgc 1441 agcacctcat cgggctgagc aatctgaccc acgtgctgta cctgtcccc ctggagagtt 1501 atgaggacat ccatggtacc ctccacctgg agaggcttgc ctatctgcat gccaggctca 1561 gggagttgct gtgtgagttg gggcggccca gcatggtctg gttagtgcc aaccctgtc 1621 ctcactgtgg ggacagaacc ttctatgacc cggagcccat cctgtgcccc tgtttcatgc 1681 ctaactagct gggtgcacat atcaaatgct tcattctgca tacttggaca ctaaagccag 1741 gatgtgcatg catcttgaag caacaaagca gccacagttt cagacaaatg ttcagtgtga 1801 gtgaggaaaa catgttcagt gaggaaaaaa cattcagaca aatgttcagt gaggaaaaaa 1861 agggaagtt ggggataggc agatgttgac ttgaggagtt aatgtgatct tggggagat 1921 acatcttata gagttagaaa tagaatctga atttctaaag ggagattctg gcttgggaag 1981 tacatgtagg agttaatccc tgtgtagact gttgtaaaga aactgttgaa aataaagaga 2041 agcaatgtga aaaaaaaaaa aaaaaaa
Tranalation of ORF (SEQ ID NO: 5):
   1 merrrlrgsi qsryismsvw tsprrlvela gqsllkdeal aiaalellpr elfpplfmaa 61 fdgrhsqtlk amvqawpftc lplgvlmkgq hlhletfkav ldgldvllaq evrprrwklq 121 vldlrknshq dfwtvwsgnr aslysfpepe aaqpmtkkrk vdglsteaeq pfipvevlvd 191 lflkegacde lfsyliekvk rkknvlrlcc kklkifampm qdikmilkmv qldsiedlev 241 tctwklptla kfspylgqmi nlrrlllshi hassyispek eegyiaqfts qflslqclqa 301 lyvdslfflr grldqllrhv mnpletlsit ncrlaegdvm hlsqspsysq lsvlslsgvm 361 ltdvspeplq allerasatl qdlvfdecgi tddqllallp slshcsqltt lafygnsisi 421 salqsllqhl iglsnlthvl ypvplesyed ihgtlhlerl aylharlrel lcelgrpsmv 481 wlsanpcphc gdrtfydpep ilcpcfmpn
```

The invention claimed is:

1. An inhibitor of PRAME and a second agent selected from the group of an inhibitor of HDAC (an HDAC) and a retinoid, as combined preparation for simultaneous, separate or sequential use in therapy, wherein the HDACi is N-hydroxy-3-(3-phenylsulfamoyl-phenyl)-acrylamide, the inhibitor of PRAME is an sRNA sequence based on a contiguous sequence of 10-30 nucleotides from the cDNA sequence of PRAME or a vector encoding said siRNA, and the therapy is treatment of a cancer expressing PRAME.

2. An inhibitor and second agent for use according to claim 1 wherein said therapy is treatment of a melanoma.

* * * * *